United States Patent
Smith

(10) Patent No.: US 8,634,900 B2
(45) Date of Patent: Jan. 21, 2014

(54) MASK COMFORT DIAGNOSTIC METHOD

(75) Inventor: David W. Smith, Oakmont, PA (US)

(73) Assignee: Koninklijke Philips N.V., Eindhoven (NL)

( * ) Notice: Subject to any disclaimer, the term of this patent is extended or adjusted under 35 U.S.C. 154(b) by 70 days.

(21) Appl. No.: 13/508,657

(22) PCT Filed: Oct. 14, 2010

(86) PCT No.: PCT/IB2010/054655
§ 371 (c)(1),
(2), (4) Date: May 8, 2012

(87) PCT Pub. No.: WO2011/058457
PCT Pub. Date: May 19, 2011

(65) Prior Publication Data
US 2012/0232403 A1    Sep. 13, 2012

Related U.S. Application Data

(60) Provisional application No. 61/260,039, filed on Nov. 11, 2009.

(51) Int. Cl.
*A61B 6/00* (2006.01)
(52) U.S. Cl.
USPC .......................... 600/474; 600/473; 382/128
(58) Field of Classification Search
USPC ................. 600/473, 474, 310; 382/128–132
See application file for complete search history.

(56) References Cited

U.S. PATENT DOCUMENTS

| 5,617,849 | A | 4/1997 | Springett |
| 6,751,340 | B2 | 6/2004 | Prokoski |
| 7,138,905 | B2 | 11/2006 | Pavlidis |
| 2007/0038042 | A1 | 2/2007 | Freeman |
| 2010/0030083 | A1 | 2/2010 | Sanders |

FOREIGN PATENT DOCUMENTS

| JP | 2009006089 | 1/2009 |
| WO | WO2008130903 A1 | 10/2008 |

OTHER PUBLICATIONS

S Scanlan et al., "Physiological Burden of the S10 Respirator", Technical Note DSTO-TN-0380, 001, XP007917136.
J Kerl et al., "Thermal Imaging of Mask Leakage During Pressure-Controlled Ventilation (Bipap Theraphy)", Somnologie, vol. 8, 2004, pp. 83-86, XP002622214.
J.G. Webster, "Prevention of Pressure Sores", The Adam Hilger Series on Biomedical Engineering, Dept of Electrical and Computer Engineering, IOP Publishing 1991, pp. 1-47.

*Primary Examiner* — Sanjay Cattungal
(74) *Attorney, Agent, or Firm* — Michael W. Haas

(57) ABSTRACT

A method of evaluating potential for discomfort of a patient (2) caused by an object (4) on the patient. The method includes acquiring (6) a first thermal image (20;40) of the patient, and wearing the object for a predetermined time. The object is removed and a plurality of thermal images (16, 24, 26, 28, 30, 44, 46, 48, 50) of the patient are acquired at predetermined times. The potential for a pressure sore or discomfort is evaluated (12) based upon at least one of the time (17) needed for one of the plurality of thermal images of the patient to return to the first thermal image, size (18) of a number of areas of an epidermis having a temperature change (19) between acquiring the first thermal image and acquiring a first one of the thermal images, and the temperature change.

15 Claims, 5 Drawing Sheets

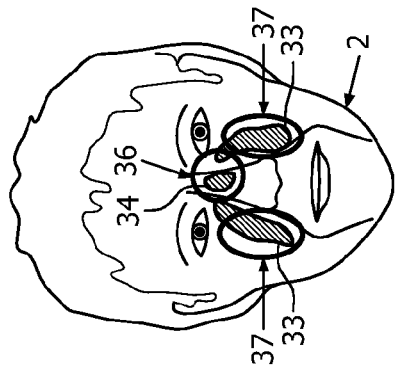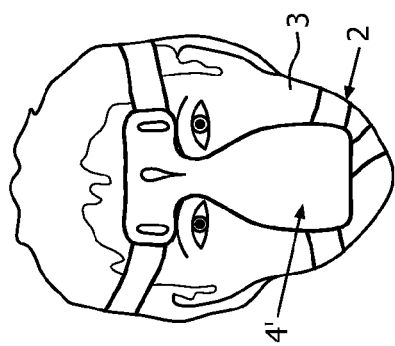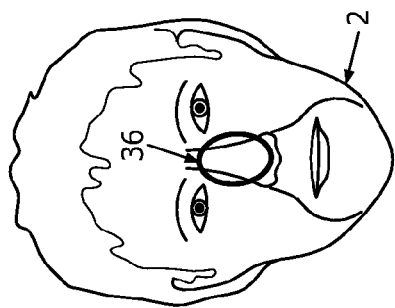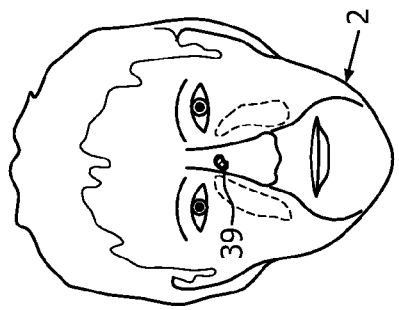

FIG. 5A  FIG. 5B  FIG. 5C
FIG. 5D  FIG. 5E  FIG. 5F

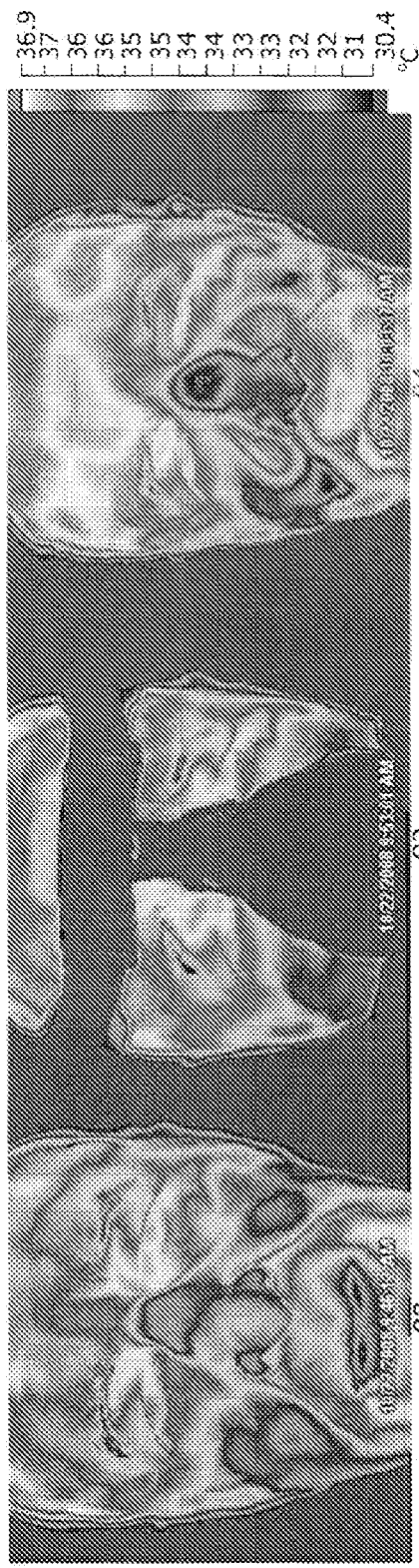
FIG. 6A  80
FIG. 6B  82
FIG. 6C  84
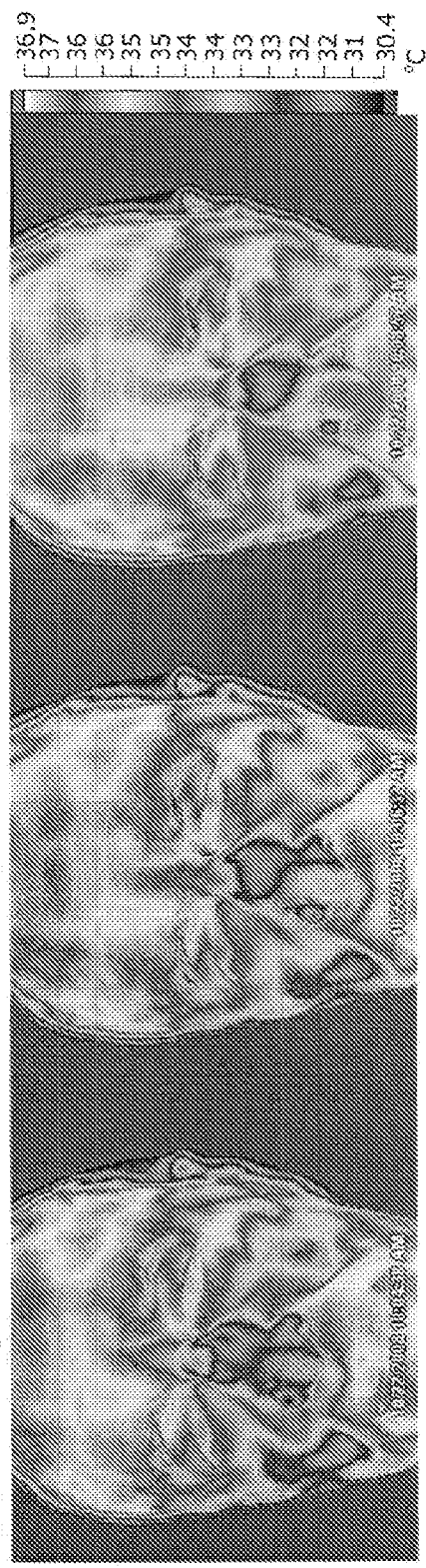
FIG. 6D  86
FIG. 6E  88
FIG. 6F  90

MASK COMFORT DIAGNOSTIC METHOD

CROSS-REFERENCE TO RELATED APPLICATIONS

This patent application claims the priority benefit under 35 U.S.C. §119(e) of U.S. Provisional Application No. 61/260,039 filed on Nov. 11, 2009, the contents of which are herein incorporated by reference.

BACKGROUND OF THE INVENTION

1. Field of the Disclosure

The invention pertains to evaluation methods for patients, and, in particular, to such methods of evaluating potential for pressure sores or discomfort of patients.

2. Description of the Related Art

In order to maximize compliance for continuous positive airway pressure (CPAP) therapy, for example, patient interface masks are designed to optimize comfort for the patient. Currently, patient comfort is assessed by return calls or follow up treatments after the patient has been on CPAP therapy for some time period.

It is generally believed that all patient interface masks generate some level of discomfort by applying pressure to the patient's face. This pressure can lead to minor red marks (e.g., a minimum level of discomfort) or open sores (e.g., a maximum discomfort). For example, it is believed that about 70% of the CPAP population gets some level of pressure sore.

Population variations add complexity to this problem. Individuals have widely varying sensitivities to mechanical pressure. Webster, J. G., "Prevention of Pressure Sores," IOP publishing (1991), pp. 1-47, discloses pressure sores caused by stagnant pressure on the skin resulting from a clinical condition. Such pressure sores include, for example, bedsores (of a bedridden patient) and sores (of a wheelchair-bound patient). Reduced blood flow is the root cause of pressure sores and varies with factors such as: vascular disease state, muscular/fatty tissue physiology, age, gender, and many other factors.

Further complexity is added from the effects of shear force. Blood flow can be reduced by both normal and shear forces applied to the skin. Most conventional pressure measurement techniques (e.g., strain based pressure sensors, thin film pressure sensors, color indicating film) do not measure shear force.

The dermis of a patient is at risk from excessive strain from pressure. The various convoluted capillary tubes can easily be bent over (e.g., kinked) by shear force which results in the occlusion of blood flow. Normal stress pressure on the capillary tubes can also cause the restriction or occlusion of blood flow.

It is known that when mechanical stress is applied to the tissues of a person having one or more conditions relating to skin temperature, age, infection, body type, collagen formation, nutrition, and fibrinolytic activity, that it is likely that a pressure sore will result. The first stage of pressure sore development affects the epidermis and can involve a circumscribed reddened area that appears bruised with no break in skin integrity. Light finger pressure can cause blanching.

SUMMARY OF THE INVENTION

Accordingly, it is an object of the present invention to provide a method that overcomes the shortcomings of conventional mask fitting methods. This object is achieved according to one embodiment of the present invention by effectively visualizing, for instance, reduced blood flow, using, for example and without limitation, high resolution thermal imaging, such that slight variations in skin surface temperature are apparent. By combining thermal imaging with time lapse techniques, it is possible to evaluate (e.g., without limitation, by a clinician; by a suitable apparatus) potential for pressure sores or discomfort of patients.

In accordance with one aspect of the invention, a method of evaluating potential for a pressure sore or discomfort of a patient caused by an object on the patient comprises: acquiring a first thermal image of the patient; wearing the object on the patient for a predetermined time; removing the object from the patient and acquiring a plurality of thermal images of the patient at predetermined times; and evaluating potential for a pressure sore or discomfort of the patient caused by the object on the patient based upon at least one of time needed for one of the plurality of thermal images of the patient to return to the first thermal image, size of a number of areas of an epidermis of the patient having a temperature change between acquiring the first thermal image and acquiring a first one of the plurality of thermal images of the patient, and the temperature change.

As another aspect of the invention, a method of evaluating potential for discomfort of a patient caused by a patient interface device on the patient comprises: acquiring a first thermal image of the patient; wearing the patient interface device on the patient for a predetermined time; removing the patient interface device from the patient and acquiring a plurality of thermal images of the patient at predetermined times; and evaluating potential for discomfort of the patient caused by the patient interface device on the patient based upon at least one of time needed for one of the plurality of thermal images of the patient to return to the first thermal image, size of a number of areas of an epidermis of the patient having a temperature change between acquiring the first thermal image and acquiring a first one of the plurality of thermal images of the patient, and the temperature change.

These and other features and characteristics of the invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIGS. 3A-3F are representations of thermal images for a patient interface mask in accordance with embodiments of the invention;

FIGS. 5A-5F are thermal images corresponding to the representations of thermal images of FIGS. 3A-3F, respectively; and FIGS. 6A-6F are thermal images corresponding to the representations of thermal images of FIGS. 4A-4F, respectively.

As employed herein, the term "number" shall mean one or an integer greater than one (i.e., a plurality). As employed herein, the term "patient" means a human being or other members of the animal kingdom. For example, a patient can be a human being who may experience any level of discomfort from any form of applied pressure.

As employed herein, the term "patient interface device" means a respiratory interface device, or a mask. As employed herein, the term "mask" means a patient interface or a patient interface mask providing or delivering air or gas flow to a patient, such as for example and without limitation, a nasal mask, an oral mask, a nasal/oral mask, a nasal pillow, a total face mark, any other device or apparatus that provides or delivers a suitable air or gas flow communicating function to a patient; or a mask employed in treating sleep disorders of a patient.

As employed herein, the term "shear force" is a stress induced by a patient interface mask or other object parallel or tangential to a surface of a patient's face or skin. As employed herein, the term "normal stress pressure" is a stress or pressure applied perpendicular to a surface of a patient's face or skin. As employed herein, the term "CPAP" means continuous positive airway pressure.

As employed herein, the terms "wear" or "wearing" mean that an object touches the epidermis of a patient. As employed herein, the terms "return", "returns" or "to return" mean that one of a plurality of thermal images is identical to or substantially similar to a prior initial (e.g., baseline) thermal image based upon a suitable clinical assessment of temperature change and/or size of an affected area. As employed here, the term "potential" means existing in possibility, or capable of development into actuality.

DETAILED DESCRIPTION OF EXEMPLARY EMBODIMENTS

Figure 1:
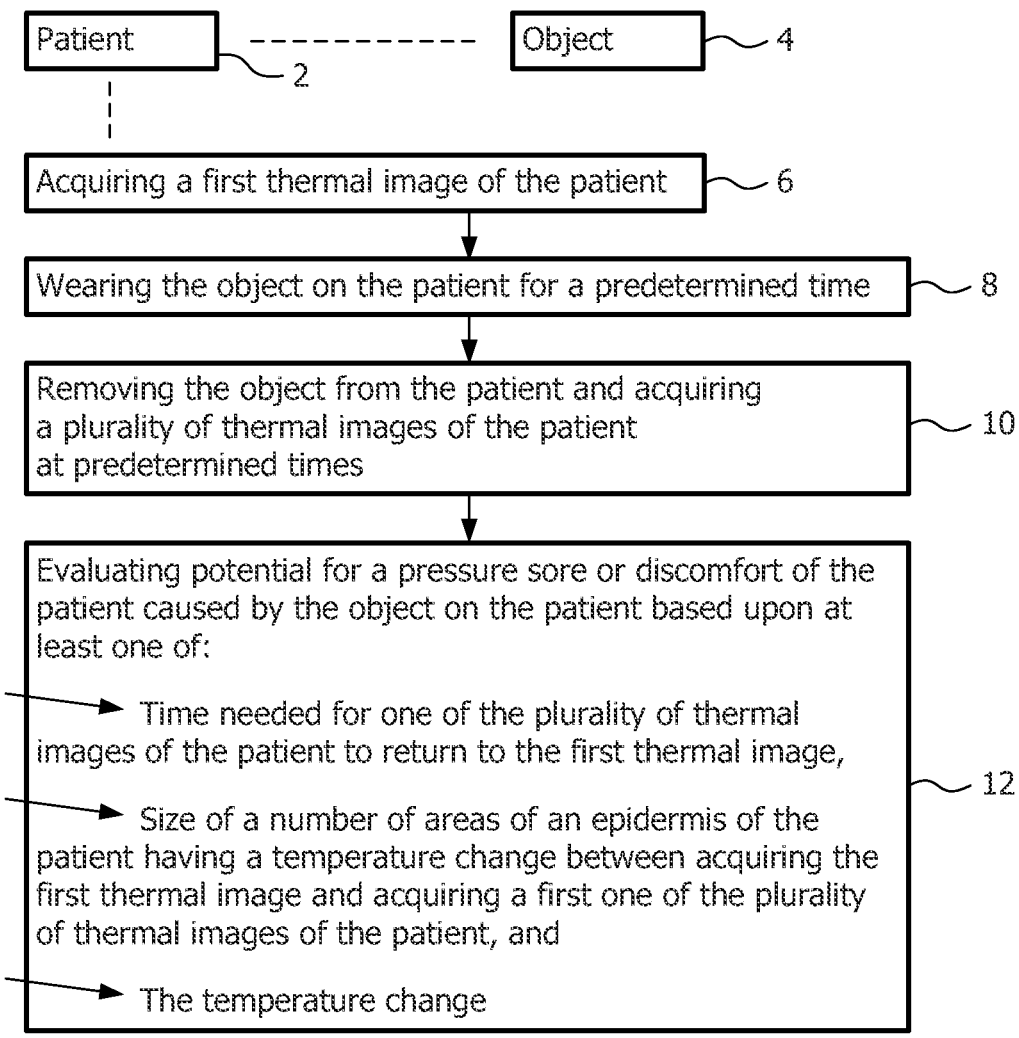
FIG. 1 is a flowchart of an evaluation method in accordance with embodiments of the invention.
Figure 2:
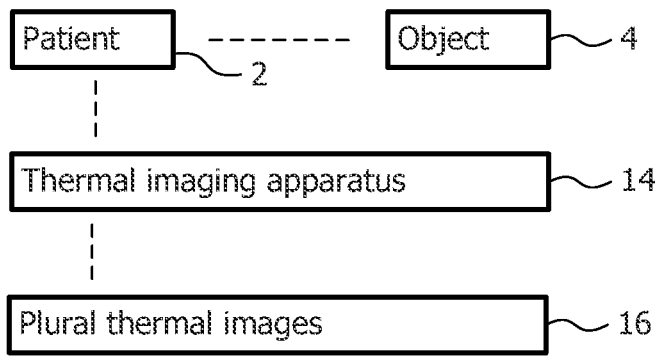
FIG. 2 is a block diagram in schematic form of thermal imaging suitable for use with the evaluation method of FIG. 1.

Referring to FIGS. 1 and 2, a method of evaluating potential for a pressure sore or discomfort of a patient 2 caused by an object 4 (e.g., without limitation, a patient interface device) on (e.g., without limitation, on the epidermis of patient 2; on a facial area of patient 2) patient 2 is disclosed. The method includes acquiring a first thermal image of patient 2, at 6; wearing object 4 on patient 2 for a predetermined time, at 8; removing object 4 from patient 2 and acquiring a plurality of thermal images of patient 2 at predetermined times, at 10; and evaluating, at 12, potential for a pressure sore or discomfort of patient 2 caused by object 4 on patient 2 based upon at least one of time 17 needed for one of the plurality of thermal images of patient 2 to return to first thermal image, size 18 of a number of areas of an epidermis of patient 2 having a temperature change 19 between acquiring the first thermal image and acquiring a first one of the plurality of thermal images of patient 2, and temperature change 19.

Example 1

Referring to FIGS. 1 and 2, the example evaluation method includes four example steps using a suitable thermal imaging apparatus 14, which provides a plurality of (e.g., without limitation, color, grayscale, raw temperature data (e.g., matrix data)) thermal images 16.

First, at 6, a baseline thermal image of patient 2 is acquired. This outlines initial temperature variations based on physiology and can be done by a clinician or an assistant, or can be automated or semi-automated.

Second, at 8, patient 2 wears object 4 (e.g., without limitation, a test mask) for a suitable predetermined time period. This predetermined time period can be timed by a clinician or an assistant, or can be automated or semi-automated.

Third, at 10, upon removal of example test mask 4, thermal images are acquired at suitable predetermined time intervals. This acquisition can be done by a clinician or an assistant, or can be automated or semi-automated.

Fourth, at 12, the time needed to return to the baseline thermal image, and the relative size and temperature change of the affected areas can all be indicators of potential pressure sores or discomfort. This evaluation can be done by a clinician, or can be automated or semi-automated. As will be described below, where the predetermined time is a first predetermined time, the evaluation can be based upon comparing at least one of time 17 needed to return to the first thermal image, size 18 of the number of the areas, and temperature change 19 with at least one of a second predetermined time, a predetermined size, and a predetermined temperature change, respectively.

A number of step 6 to acquire the first thermal image of patient 2, step 8 to time object 4 on patient 2 for the predetermined time, step 10 to acquire the plurality of thermal images of patient 2 at the predetermined times, and step 12 to evaluate the potential for the pressure sore or the discomfort of patient 2 caused by object 4 on patient 2 can be automated.

Example 2

Steps 6,8,10,12 can, for example, be fully automated in the form of an example kiosk (not shown). For example, a "picture booth" type kiosk (not shown) can employ indicators for what to do to acquire the baseline thermal image of patient 2, when to initially put example test mask 4 on patient 2, when to take the example test mask 4 off patient 2, what to do to acquire thermal images at predetermined time intervals, and optionally when the testing is concluded after a thermal image returns to baseline thermal image of step 6. For example, suitable equipment (not shown) can time and decide that the thermal image returns to the baseline thermal image by employing suitable automatic image comparison tools (not shown) and/or facial recognition software (not shown). Such equipment can also determine the relative size and temperature change of the affected areas as indicators of potential pressure sores or discomfort by employing suitable automatic image analysis tools (not shown).

Example 3

The predetermined time period of step 8 can be as short as about 5 minutes to about 10 minutes, the latter of which is the approximate time corresponding to representations of thermal images 20, 22, 24, 26, 28, 30 of FIGS. 3A-3F and representations of thermal images 40, 42, 44, 46, 48, 50 of FIGS. 4A-4F. Example thermal images 60, 62, 64, 66, 68, 70 are shown in FIGS. 5A-5F corresponding to respective FIGS. 3A-3F, and example thermal images 80, 82, 84, 86, 88, 90 are shown in FIGS. 6A-6F corresponding to respective FIGS. 4A-4F.

Example 4

While relatively shorter time periods than that of Example 3 are possible, the reliability of the measurement would drop accordingly.

Example 5

Preferably, relatively longer time periods than that of Example 3 are employed. One example application is in connection with a sleep lab setting where thermal images are taken in the evening before a patient goes to sleep, and again in the morning upon removal of example test mask 4 of FIG. 1. Here, for example, the predetermined time of step 8 is a time interval defined between a first time in an evening and a second later time in a subsequent morning.

Example 6

The predetermined time intervals of step 10 of FIG. 1 are preferably long enough to visualize changes in thermal images 16 of FIG. 2. Such times can be related to the time that patient 2 wears example test mask 4.

Example 7

For example, if example test mask 4 of FIG. 1 is worn for an example 10-minute period, then the blood flow of the patient 2 recovers relatively quickly and the thermal images of step 10 are taken, for example and without limitation, about every 30 seconds, about every 1 minute, or at any suitable periodic or repetitive interval.

Example 8

As another example, when patient 2 wears example test mask 4 of FIG. 1 for a relatively longer time (e.g., without limitation, overnight), then marks can remain on the skin (i.e., epidermis) of patient 2 for a number of hours. In this case, 30-second or 1-minute time intervals are impractical, and the time of step 10 can be increased to between about 5 minutes to about 10 minutes.

Example 9

Decision criteria for step 12 of FIG. 1 generally employs some level of clinical judgment, but a suitable thermal image comparison approach can be employed to look for differences between "before" and "after" thermal images.

Example representations of thermal images 20, 22, 24, 26, 28, 30 of FIGS. 3A-3F and 40, 42, 44, 46, 48, 50 of FIGS. 4A-4F are shown for two different example types of test masks 4',4". Both representation sets of FIGS. 3A-3F and 4A-4F involve wearing a corresponding object (e.g., test masks 4' and 4") on epidermis 3 of patient 2 for a predetermined time; and evaluating the potential for a low level pressure sore or discomfort of patient 2 caused by corresponding object 4',4" on epidermis 3 of the patient 2.

Example 10

FIG. 3A shows representation 20 of the baseline thermal image. FIG. 3B is representation 22 of a thermal image taken when first example test mask 4' is applied with air pressure. FIG. 3C is representation 24 of a thermal image taken immediately after removal of first example test mask 4', which was about 9 or 10 minutes after first example test mask 4' was applied. This shows a significant size and severity of temperature drop 34 at a bony nose bridge area 36 with respect to baseline representation 20 of FIG. 3A. This also shows a slight temperature rise 33 in two soft tissue areas 37. FIGS. 3D-3F show representations 26, 28, 30 of thermal images taken at about one minute example intervals after the first example test mask 4' was removed in FIG. 3C.

FIG. 3D shows that temperature drop 34 of FIG. 3C is followed by a temperature rise 38 (or "hot spot") in area 36. FIG. 3E shows a relatively smaller area with a reduced temperature rise 39 as compared to temperature rise 38 of FIG. 3D. Over time, as shown in FIG. 3F, the entire thermal image area (e.g., at area 36) returns to representation 20 of the baseline thermal image (FIG. 3A).

Example 11

Figure 4C:
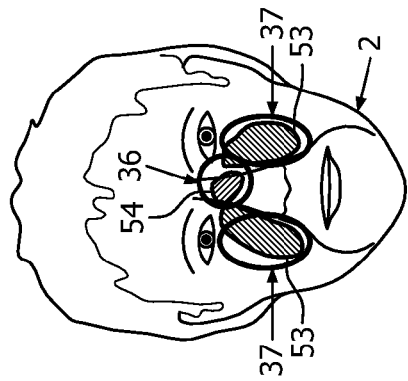
FIGS. 4A-4F are representations of thermal images for another patient interface mask in accordance with other embodiments of the invention.
Figure 4F:
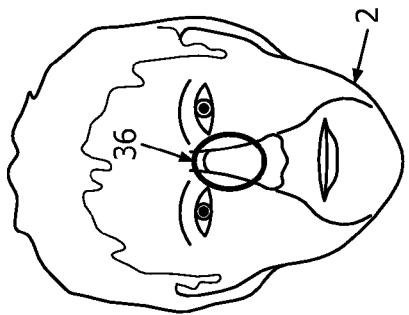
Figure 4B:
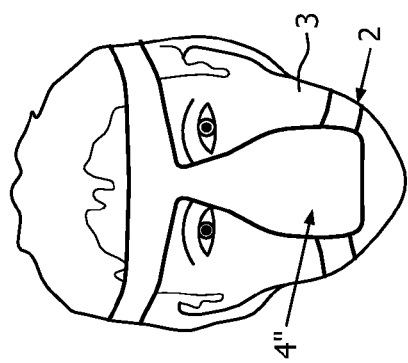
Figure 4E:
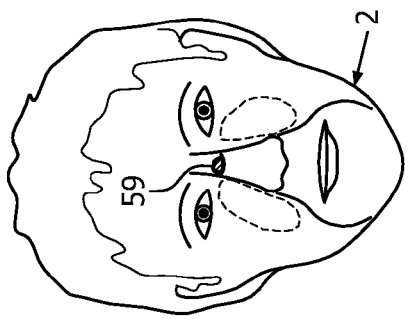
Figure 4A:
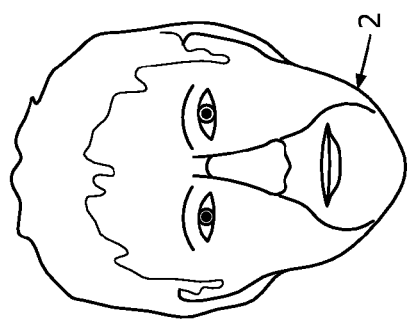
Figure 4D:
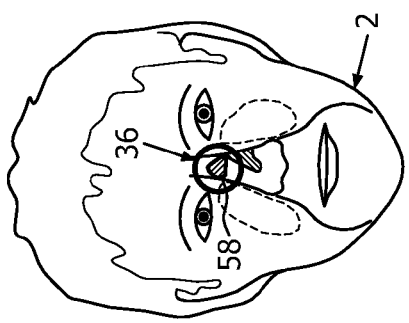

FIG. 4A shows representation 40 of another baseline thermal image, which can be, for example, the same as or similar to representation 20 of FIG. 3A. FIG. 4B is representation 42 of a thermal image taken when second example test mask 4" is applied with air pressure. FIG. 4C is representation 44 of a thermal image taken immediately after removal of second example test mask 4", which was about 10 or 11 minutes after second example test mask 4" was applied. This shows a significant size and severity of temperature drop 54 at area 36 with respect to baseline representation 40 of FIG. 4A. FIGS. 4D-4F show representations 46, 48, 50 of thermal images taken at about one example minute, three example minutes and five example minutes, respectively, after second example test mask 4" was removed in FIG. 4C. FIG. 4D shows that temperature drop 54 of FIG. 4C is followed by a temperature rise 58 (or "hot spot") in area 36. FIG. 4E shows a relatively smaller area with a reduced temperature rise 59 as compared to temperature rise 58 of FIG. 4D. Over time, as shown in FIG. 4F, the entire thermal image area (e.g., at area 36) returns to baseline representation 40 (FIG. 4A). This shows how a clinician or assistant can decide that representation 50 returns to baseline representation 40.

Example 12

From previous representations 20, 22, 24, 26, 28, 30 and 40, 42, 44, 46, 48, 50 of FIGS. 3A-3F and 4A-4F (e.g., thermal images 60, 62, 64, 66, 68, 70 and 80, 82, 84, 86, 88, 90 of FIGS. 5A-5F and 6A-6F), a clinician can conclude that first example test mask 4' (FIGS. 3A-3F) should be relatively more comfortable overall for this particular patient 2 than the other example test mask 4". This particular conclusion can be based, for example, upon one, two or three example factors: (1) the relative temperature rise from baseline at a predetermined time (there being no difference in this particular example); (2) there is a relatively smaller effected area 34 and 38 versus 54 and 58 at nose bridge area 36 (which is a known sensitive area); and (3) there is a relatively faster time to return to baseline representation 20 than to the other baseline representation 40.

These three factors are shown in Table 1, in which two of the example factors are different. It will be appreciated that an evaluation can be based upon one, two or all three of the example factors by comparing the time needed to return to first baseline representation 20 (FIG. 3A), the size of the number of areas 34 and 38, and the temperature change 19 (FIG. 1) with a second predetermined time, a predetermined size, and a predetermined temperature change, respectively. There, the second predetermined time, the predetermined size, and the predetermined temperature change are based upon representations 40, 42, 44, 46, 48, 50 of thermal images of FIGS. 4A-4F. In this example, the comparison determines that a first patient interface device (e.g., first example test mask 4') is relatively more comfortable for the patient than a different second patient interface device (e.g., second example test mask 4"). In these mask-to-mask comparisons, a suitable comparison can be made, for example, by assessing, for example, representations 24 of FIGS. 3C and 44 of FIG. 4C only (e.g., for size and/or temperature change).

TABLE 1

|  | Temperature rise from baseline at 1 minute | Relative size of temperature rise area at 1 minute | Time to return to baseline |
|---|---|---|---|
| First mask 4' | +2° C. | Smaller | 3 minutes |
| Second mask 4" | +2° C. | Larger | 5 minutes |

Examples 13 to 15 discuss example uses for the disclosed evaluation method including mask-to-mask comparisons, checking for proper mask fit, and individual sensitivity checking.

Example 13

When developing new masks, design engineers need to understand how a prototype mask compares to known production patient interface devices, such as known production masks. Suitable mask-to-mask comparisons can be made between two masks (e.g., a prototype mask and a known production mask) by having a trial population wear each mask, and by comparing the overall temperature rise, size of the effected area, and time to return to baseline metrics as were discussed, above, in connection with Example 12. For example, this can determine whether a particular object (e.g., without limitation, a prototype mask; a prototype patient interface device; a different patient interface device) is appropriate for a particular patient or for the general population. For example, the second predetermined time, the predetermined size, and the predetermined temperature change can be operatively associated with the production patient interface device for a plurality of different patients. Based upon the comparison, as was discussed above in connection with Example 12, the comfort of the prototype patient interface device can be evaluated versus the comfort of the production patient interface device.

Example 14

Sleep laboratories spend considerable time and effort matching, for example, CPAP masks to patients, and making the proper CPAP mask positional adjustments. This effort is employed to maximize patient comfort while still ensuring proper sealing characteristics. This effort is difficult because, in many cases, a fit cannot properly be evaluated until a patient sleeps with a CPAP mask for an extended time period (e.g., without limitation, several nights). In contrast, the disclosed evaluation method can relatively quickly evaluate if a patient is likely to be successful with a specific mask, and the corresponding mask positional adjustments (e.g., adjusting a predetermined patient interface mask, such as a CPAP mask, for fit on the epidermis of the patient) for that patient with the specific mask. Hence, the disclosed evaluation method enables checking for proper mask fit by evaluating mask adjustment and fit of the CPAP mask on the patient. For example, the second predetermined time, the predetermined size, and the predetermined temperature change can be operatively associated with the same or similar CPAP mask as adjusted for fit for a plurality of different patients. Based upon the comparison, as was discussed above in connection with Example 12, the proper fit of the example CPAP mask can be evaluated versus the comfort of the same or similar CPAP mask for a general population.

Example 15

Individual patients have widely varying degrees of sensitivity to facial pressure. Furthermore, sensitivity to facial pressure will vary across specific facial areas. For example, mid nose area 36 may be relatively more sensitive to pressure than cheek area 37. By mounting a "standard" mask on a patient, a clinician can employ the disclosed evaluation method to understand and check the level of individual sensitivity for one patient as compared to other different patients (e.g., a general population). This enables the determining of whether the patient is sensitive to pressure caused by the "standard" mask, which has been evaluated across other different patients.

Example 16

A non-limiting example of an apparatus, device or camera used to acquire the example thermal images 60, 62, 64, 66, 68, 70 and 80, 82, 84, 86, 88, 90 of FIGS. 5A-5F and 6A-6F is a Fluke® Ti50-FT20 thermal imaging camera with IR-Fusion® Technology, as marketed by Fluke Corporation of Everett, Wash. It will be appreciated, however, that this is an example and any suitable thermal imaging apparatus can be employed. Some other example suppliers include FUR Systems of Boston, Mass., and Sierra Pacific Innovations Corp. of Las Vegas, Nev.

Example 17

The invention is disclosed in connection with patient interface masks for CPAP applications, but can also be applied to a wide range of situations or applications where pressure is applied to the skin of a patient. Some typical non-limiting uses for patient interface masks include application of pressure support therapy for the treatment of sleep apnea. For such an application, the patient wears the mask while sleeping every night indefinitely. Patient interface masks can also be used for active ventilation in certain hospital settings. Other non-limiting examples include gas masks (e.g., without limitation, ventilation; fire; scuba; hazmat), masks supporting headgear; other applications where long term mask use is needed; a pair of eyeglasses; jewelry; relatively tight fitting clothing; or any application where pressure is applied to the skin. Significant work has been done in this area as it relates to decubitus ulcers (bedsores). Examples of this are bedridden patients in a hospital environment or wheelchair bound patients. In the disclosed embodiments, the pressure applied to the skin is generally lower in magnitude and shorter in time. This does not normally lead to the significant open wounds found in a clinical setting.

The disclosed invention is applicable to "pressure sore" evaluation and/or "comfort" evaluation. Comfort is a relatively subtle measurement that can involve relatively small changes in skin temperature (e.g., without limitation, a change of a number of ° C.), which can be empowered by modern thermal imaging technology.

Although the invention has been described in detail for the purpose of illustration based on what is currently considered to be the most practical and example embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the invention contemplates that, to the extent possible, one or more features of any embodiment can be combined with one or more features of any other embodiment.

What is claimed is:

1. A method of evaluating potential for a pressure sore or discomfort of a patient caused by an object on the patient, the method comprising:
   acquiring a first thermal image of the patient;
   wearing the object on the patient for a predetermined time interval;
   removing the object from the patient and acquiring a plurality of thermal images of the patient at predetermined times; and
   evaluating potential for a pressure sore or discomfort of the patient caused by the object on the patient based upon at least one of time interval needed for one of the plurality of thermal images of the patient to return to the first thermal image, and size of a number of areas of an epidermis of the patient having a temperature change between acquiring the first thermal image and acquiring a first one of the plurality of thermal images of the patient.

2. The method of claim 1, further comprising:
   employing, as the predetermined time interval, a first predetermined time interval; and
   comparing at least one of the time interval needed to return to the first thermal image, and the size of the number of the areas with at least one of a second predetermined time interval, and a predetermined size, respectively.

3. The method of claim 2, further comprising:
   (a) evaluating adjustment and fit of the object on the patient;
   (b) determining whether the object is appropriate for the patient; or
   (c) determining whether the patient is sensitive to pressure caused by the object.

4. The method of claim 1, further comprising:
   employing, as the predetermined time interval, a first predetermined time interval; and
   comparing the time interval needed to return to the first thermal image, and the size of the number of the areas with a second predetermined time interval, and a predetermined size, respectively.

5. The method of claim 4, further comprising:
   evaluating adjustment and fit of the object on the patient;
   determining whether the object is appropriate for the patient; or
   determining whether the patient is sensitive to pressure caused by the object.

6. The method of claim 4, further comprising:
   employing a first patient interface device as the object;
   employing a different second patient interface device operatively associated with the second predetermined time interval, and the predetermined size; and
   determining whether the first patient interface device or the different second patient interface device is relatively more comfortable for the patient based upon the comparing.

7. The method of claim 6, further comprising:
   employing a prototype patient interface device as the first patient interface device;
   employing a production patient interface device as the different second patient interface device;
   employing the second predetermined time interval, and the predetermined size operatively associated with the production patient interface device for a plurality of different patients; and
   evaluating comfort of the prototype patient interface device versus comfort of the production patient interface device based on the comparing.

8. The method of claim 1, further comprising:
   employing a predetermined patient interface mask as the object;
   employing as the predetermined time interval a first predetermined time interval;
   comparing the time interval needed to return to the first thermal image, and the size of the number of the areas with a second predetermined time interval, and a predetermined size, respectively; and
   employing the second predetermined time interval, and the predetermined size operatively associated with the predetermined patient interface device for a plurality of different patients.

9. The method of claim 1, further comprising employing a time interval defined between a first time in an evening and a second later time in a subsequent morning as the predetermined time interval.

10. The method of claim 2, further comprising:
    employing a predetermined patient interface mask (4';4") as the object;
    adjusting the predetermined patient interface mask for fit on the epidermis of the patient; and
    checking for proper fit of the adjusted predetermined patient interface mask based upon the comparing.

11. The method of claim 1, further comprising automating a number of the acquiring the first thermal image of the patient, timing the object on the patient for the predetermined time interval, the acquiring the plurality of thermal images of the patient at the predetermined times, and the evaluating the potential for the pressure sore or the discomfort of the patient caused by the object on the patient.

12. The method of claim 1, further comprising:
    wearing the object on the epidermis of the patient for the predetermined time interval; and
    evaluating the potential for a low level pressure sore or the discomfort of the patient caused by the object on the epidermis of the patient.

13. The method of claim 1, further comprising: acquiring the first thermal image of the patient and acquiring the plurality of thermal images of the patient using a thermal imaging apparatus.

14. A method of evaluating potential for discomfort of a patient on the patient, the method comprising:
    acquiring a first thermal image of the patient;
    wearing the patient interface device on the patient for a predetermined time interval;
    removing the patient interface device from the patient and acquiring a plurality of thermal images of the patient at predetermined times; and
    evaluating potential for discomfort of the patient caused by the patient interface device on the patient based upon at least one of time interval needed for one of the plurality of thermal images of the patient to return to the first thermal image, and size of a number of areas of an epidermis of the patient having a temperature change between acquiring the first thermal image and acquiring a first one of the plurality of thermal images of the patient.

15. The method of claim 14, further comprising acquiring the thermal images of the patient at the predetermined times until the one of the plurality of thermal images returns to the first thermal image.

* * * * *